(12) United States Patent
Schraga

(10) Patent No.: US 6,514,270 B1
(45) Date of Patent: Feb. 4, 2003

(54) SINGLE USE LANCET DEVICE

(76) Inventor: Steven Schraga, 9433 Byron Ave., Surfside, FL (US) 33154

( * ) Notice: Subject to any disclaimer, the term of this patent is extended or adjusted under 35 U.S.C. 154(b) by 0 days.

(21) Appl. No.: 09/709,738

(22) Filed: Nov. 10, 2000

(51) Int. Cl.[7] ............................................. A61B 17/14
(52) U.S. Cl. ...................................... 606/182; 606/181
(58) Field of Search ............................... 606/181, 182, 606/183, 184, 185; 604/136

(56) References Cited

U.S. PATENT DOCUMENTS 5,147,375 A  *  9/1992  Sullivan et al. ............. 606/182
5,908,434 A  *  6/1999  Schraga ....................... 606/182

* cited by examiner

Primary Examiner—Kevin T. Truong

(74) Attorney, Agent, or Firm—Malloy & Malloy, P.A.

(57) ABSTRACT

A single use lancet device having a housing, a lancet with a piercing tip movably disposed in the housing and structured to move between a cocked orientation and a piercing orientation, and a driving assembly structured to move the lancet into the piercing orientation. A retention member and an engagement hub are further provided and structured to be cooperatively engaged with one another upon the lancet being disposed in the cocked orientation so as to maintain the lancet in the cocked orientation until released by an actuation assembly. Specifically, the actuation assembly is structured to move between an actuated and an un-actuated orientation, movement into the actuated orientation releasing the retention member and the engagement hub from their cooperative engagement with one another and thereby result in movement of the lancet into the piercing orientation. The device also includes a restrictor assembly structured to substantially prevent the actuation assembly from moving out of the actuated orientation, thereby preventing re-firing of the lancet utilizing the actuation assembly.

18 Claims, 1 Drawing Sheet

SINGLE USE LANCET DEVICE

BACKGROUND OF THE INVENTION

1. Field of the Invention

The present invention relates to a single use lancet device structured to be conveniently and effectively utilized for various blood sampling procedure, but which is also substantially safe, preventing re-firing of the device after it has been used, and thereby preventing and/or substantially minimizing inadvertent contamination of a patient and/or other personnel as a result of a used and potentially contaminated lancet. Furthermore, the device is compact and easy to utilize in a cost effective and preferably fully disposable manner.

2. Description of the Related Art

Lancets are commonly utilized instruments which are employed both in hospitals and other medical facilities, as well as by private individuals, such as diabetics, in order to prick or pierce a patient's skin, typically on a finger of a patient, thereby leading to the generation of a blood sample which can be collected for testing. Because of the wide spread use of such lancets, there are a variety of lancet devices which are available for utilization by patients and/or practitioners in a variety of different circumstances.

For example, a typical lancet may merely include a housing with a sharp piercing tip that is pushed into the patient's skin. More commonly, however, lancet devices, which house a piercing tip and/or a lancet, have been developed which effectively encase and fire the lancet into the patient's skin, thereby eliminating the need for the person taking the sample to actually push the lancet tip into the skin.

Within the various types of specialized lancet devices, one variety are typically configured for multiple and/or repeated uses, while another category is particularly configured for single use, after which the entire device is disposed of. Looking in particular to the single use, disposable lancet devices, such devices typically include a housing which contains and directs or drives a piercing tip into the patient's skin, and which is disposed of along with the used lancet. Naturally, so to make such disposable devices cost effective for frequent use, such devices tend to be rather simplistic in nature providing only a sufficient mechanism for firing, and not overly complicating the design so as to minimize that cost.

While existing single use devices are generally effective for achieving the piercing of the skin required for effective operation, such single use, disposable devices typically do not incorporate a large number of safety features to ensure the safe use and disposal of the device. For example, one primary area of safety which must be addressed with all lancet devices pertains to the purposeful and/or inadvertent reuse of a contaminated lancet. Unfortunately, most currently available single use lancet devices are configured such that after a use thereof has been achieved, it is possible for a patient to re-cock the device, thereby allowing for a subsequent, inappropriate use.

As a result, it would be highly beneficial to provide a single use lancet device which is substantially compact and disposable, can be manufactured in a substantially cost effective manner, and which nevertheless is substantially safe to utilize, affirmatively preventing re-use, once contaminated. Additionally, it is noted that while other devices may be provided to prevent the lancet form even being cocked, it would still be beneficial to provide a device that even if the lancet is re-cocked does not allow for additional and/or secondary firing.

SUMMARY OF THE INVENTION

The present invention is direct to a single use lancet device of the type commonly utilized for various blood sampling purposes. In particular, the single use lancet device of the present invention includes a housing and a lancet. The lancet, which also includes a piercing tip, is movably disposed in the housing and is structured to move at least between a cocked orientation and a piercing orientation. A drive assembly is provided so as to actually move the lancet at least temporarily into the piercing orientation.

In order to retain the lancet in the cocked orientation, the illustrated embodiment of the single use lancet device of the present invention includes a retention member and a engagement hub. In particular, the engagement hub is structured to be cooperatively engaged with the retention member, at least when the lancet is disposed in the cocked orientation. As a result, the retention member and the engagement hub, which are cooperatively engaged with the housing and the lancet, effectively maintain the lancet in the cocked orientation until they are released from that engagement with one another. As such, it is seen, in this embodiment, that when the lancet is ready for use, it is maintained in the cocked, ready to fire orientation until that time.

In order to release the lancet, and more particularly the cooperative engagement between the retention member and the engagement hub of the illustrated embodiment, the present invention further includes an actuation assembly. Specifically the actuation assembly is structured to move between an actuated and an un-actuated orientation. In this regard, movement of the actuation assembly into the actuated orientation is structured to release at least the retention member and the engagement hub from their cooperative engagement with one another, thereby resulting in movement of the lancet into the piercing orientation.

In order to substantially minimize the inadvertent re-use of the single use lancet device of the present invention, a restrictor assembly is also preferably provided. Specifically, the restrictor assembly is structured to substantially prevent the actuation assembly from moving out of the actuated orientation, at least after the lancet has moved at least temporarily into the piercing orientation. In this regard, the restrictor assembly may include an abutment structure that is cooperatively disposed between the housing and a release element of the actuation assembly that actually releases the retention member and the engagement hub from their cooperative engagement with one another. As such, once the lancet device of the present invention has been fired the actuation assembly cannot move back into its un-actuated orientation for a subsequent firing, regardless of whether the lancet itself may or may not be moved back into the cocked orientation.

These and other features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
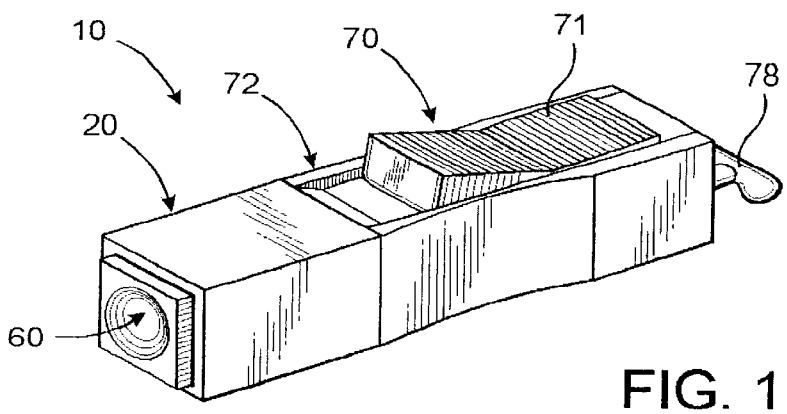
FIG. 1 is a rear perspective illustration of the single use lancet device of the present invention.

Shown throughout the Figures, the present invention is directed towards a single use lancet device, generally indicated as 10. In particular, the lancet device 10 is utilized to help facilitate the taking of a blood sample, such as may be commonly performed by diabetics and/or by medical personnel. In this regard, the single use lancet device is structured to prick a portion of the patient's body, such as commonly the finger, resulting in a small amount of bleeding which can be collected for sampling and subsequent testing.

Looking in particular to the single use lancet device 10 of the present invention, it includes a housing 20. The housing 20 is preferably generally in small and compact in shape so as to facilitate manipulation and grasping by a user. Furthermore, the housing 20 may be constructed from any of a variety of materials, although plastic may be the most commonly used material for ease in manufacture and/or cost effectiveness. The housing 20 includes an open interior 22, and at least a piercing opening 26. The piercing opening 26 provides access to the opening interior 22, such as at an end of the housing 20.

Contained at least partially within the open interior 22 of the housing 20 is a lancet 30. Specifically, the lancet 30 includes a piercing tip 32 which will actually and ultimately emerge from the housing 20 and result in the piercing of the patients skin for the required bleeding. In this regard, the present invention is described in the context of a single use lancet device 10, and preferably a fully disposable single use lancet device 10. As such, the lancet 30 in the illustrated embodiment is preferably a self contained and generally integral element within the housing 20, perhaps including a separate metal piercing shaft. It is of course, understood, however, that as is the case with many re-useable lancet devices, it is possible for a more elaborate lancet assembly to be provided within the primary housing 20, the lancet 30, which in includes the piercing tip 32, being disposed within a corresponding receiving assembly and moving therewith within the primary housing 20. As such, one or a plurality of components may indeed ultimately comprise the lancet 30, although a single integral device is disclosed with regard to the illustrated embodiment.

Figure 2:
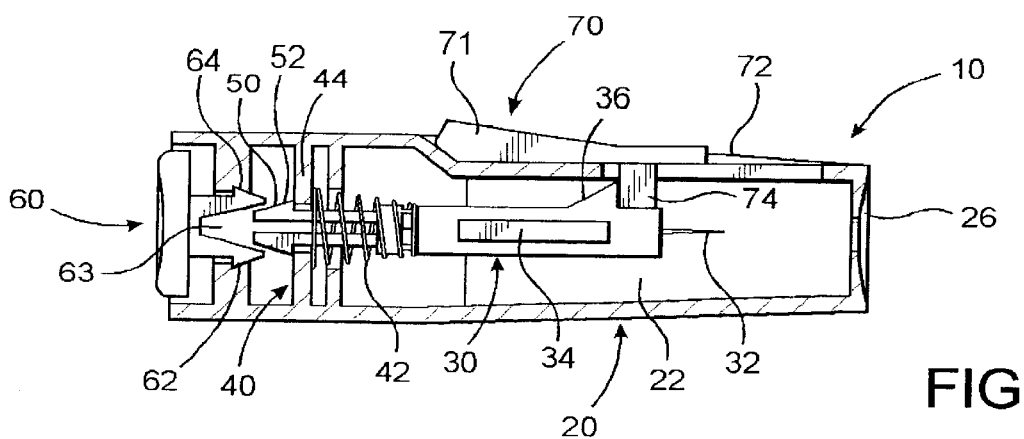
FIG. 2 is a side cross-section view of an embodiment of the single use lancet device of the present invention illustrating the lancet in the cocked orientation, and the actuation assembly in the un-actuated orientation.
Figure 3:
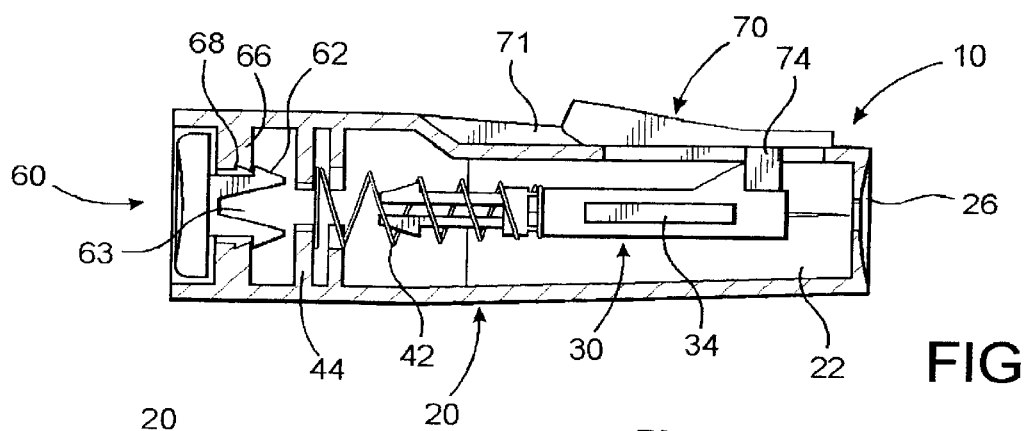
FIG. 3 is a side cross-section view of the embodiment of FIG. 2 illustrating the lancet temporarily disposed in the piercing orientation, and illustrating the actuation assembly disposed in the actuated orientation.

As indicated, the lancet 30 is structured to move within the housing 20 and is structured to move at least from a cocked orientation, as illustrated in FIG. 2, to a piercing orientation, as illustrated in FIG. 3. The cocked orientation of FIG. 2 is characterized generally by the lancet 30 being withdrawn within the housing 20, and being ready to be fired. Conversely, the piercing orientation, as in FIG. 3, is characterize generally by the piercing tip 32 of the lancet 30 protruding at least partially from the piercing opening 26 of the housing 20. In this regard, and for safety purposes it is preferred that the piercing orientation of FIG. 3 be only temporarily maintained to achieve piercing of the finger, and that the normal movement of the lancet 30 result in its eventually residing in a retracted, although not cocked orientation concealed within the housing 20. Also along these lines, it is recognized that the lancet 30 may be provided initially to users in a pre-cocked orientation, or as in the illustrated embodiment, may be provided in a retracted or concealed orientation which allows for the ultimate user to actually move the lancet 30 into the cocked orientation prior to actual use. In all such instances of movement, it is recognized as illustrated in the Figures, that the lancet 30, if desired may include one or more protrusions 34 defined thereon so as to help to guide a generally straight and/or linear path of movement of the lancet 30. Of course, such structure is not necessarily required.

Figure 4:
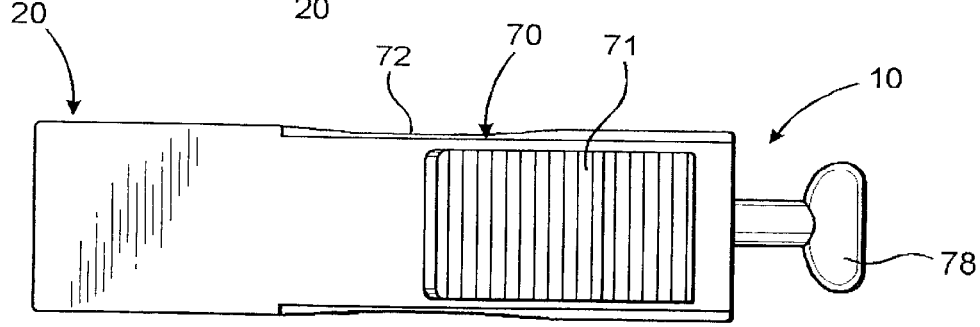
FIG. 4 is a top plan view of the single use lancet device of the present invention illustrating an embodiment of the cocking assembly.

As seen in FIG. 4, a protective shields 78 may also preferably be positioned over the piercing tip 32 of the lancet 30 prior to ultimate use of the single use lancet device 10 of the present invention. Naturally, this protective guard 78, which may be separately or integrally formed with the remainder of the lancet 30, is preferably disposed in concealing relation to the piercing tip, and when the lancet 30 is moved into the cocked orientation is removed, thereby exposing the piercing tip for use. Although it is possible that the protective shield 78 may be maintained on the piercing tip 32 even when the lancet 30 is in the cocked orientation, in the illustrated embodiment, the protective shield 78 preferably includes a generally large head such that when the lancet 30 is moved into the cocked orientation, the protective shield 78 tends to be removed, either on its own, or with only a small degree of assistance by the user. Certainly, more affirmative removal may also be required.

In order to move the lancet 30 into the aforementioned cocked orientation, a cocking assembly 70 is provided. In particular, the cocking assembly 70 includes a cocking element 71 that is structured to be manipulated by a user. Specifically, the cocking element 71 preferably protrudes from the housing 70 and may, if desired, slide along at least a portion of the length of the housing 20, such as within one or more tracks 72. Moreover, as in the illustrated embodiment, a generally sloped and potentially notched configuration may be provided for the cocking element 71 so as to facilitate manipulation by a user in an effective and convenient manner. As best seen in FIGS. 2 and 3, the cocking element 71 preferably extends from within the housing 20, protruding to the exterior for manipulation by the user. In protruding from the housing 20, however, the cocking element 71 also includes an inwardly depending abutment 74. Specifically, the inwardly depending abutment 74 is preferably structured to engage the lancet 30 and may be structured to engage a corresponding protrusion 36 on the lancet 30. As such, at least upon rearward movement of the cocking element 71, the lancet 30 is also moved backwards to a cocked orientation. Further, it is recognized that the cocking element 71 may be integral with the lancet 30 and/or may be a separate component, as in the illustrated Figures.

Looking now in further detail to the positioning of the lancet 30 in the cocked orientation of FIG. 2, as indicated, it is preferred that the lancet 30 will be disposed and generally held in that cocked orientation until affirmatively released, as will be described. In the illustrated embodiment, the present invention includes a retention member and an engagement hub that are cooperatively engaged with one another when the lancet 30 is disposed in the cocked orientation so as to maintain the lancet 30 in the cocked orientation until released. Also in the illustrated embodiment, the retention member includes at least one finger 50 that extends from and/or may be integrally formed with the remainder of the lancet 30. Conversely, the engagement hub 44 is defined in connection with the housing 20 and is preferably a rigid, cooperative structure. In this regard, the one and preferably two fingers 50 of the illustrated retention member preferably include a generally biased configuration structured to somewhat compress and thereby allow passage through an opening defined by the engagement hub 44. Once the tips of the fingers 50 have passed beyond the engagement hub 44, a depending protrusion 52, that is preferably disposed on each of the fingers 50, may abut the engagement hub 44 thereby preventing passage of the lancet 30 out of the cocked orientation until released.

The present single use lancet device 10 includes a drive assembly, generally indicated as 40. In the illustrated embodiment, the drive assembly 40 includes a biasing element 42, such as a spring, which engages an appropriate surface in the primary housing 20. Also in the illustrated embodiment, the engagement hub 44 also acts as the abutment surface for the spring 42. As such, when the lancet 30 is moved towards and into the cocked orientation, a compression of the biasing element 42 results. Moreover, because the finger(s) 50 preferably includes a generally sloped or tapered tip configuration, it is urged towards and into the opening in the engagement hub 44, the finger(s) 50 generally compressing towards the center of the housing for effective passage beyond the engagement hub 44. Once the finger(s) 50 have passed a sufficient distance, the finger(s) 50 will flair outwardly generally towards there normal position and the depending protrusion 52 will abut the engagement hub 44. Accordingly, despite the compressed tension of the biasing element 42, the tip of the fingers 50 are held from the engagement hub 44 by the depending protrusions 52.

In order to provide for the effective release of the lancet 30 from its cocked orientation, the present invention further includes an actuation assembly 60. Specifically, the actuation assembly 60 is structured to be manipulated and/or actuated by a user in order to effectively release the lancet 30 from its cocked orientation. In this regard, the actuation assembly 60 is structured to move between an un-actuated orientation as in FIG. 2, to an actuated orientation, as in FIG. 3. The actuation assembly 60 includes an exterior or head portion, which is structured to be effectively manipulated, and in particular pushed, by the user. Further, the actuation assembly 60 includes an interior release element 62 that extends into the housing. The release element(s) 62 of the actuation assembly 60 preferably includes a generally stiff, but still at least slightly biased configuration, and a gap 63 defined thereby. Specifically, the gap 63 is disposed such that the tip of the fingers 50 of the retention member may pass therein as the actuation assembly 60 is moved into its actuated orientation. In particular, the release elements 62 are structured and disposed such that corresponding surfaces thereof engage the tips of the fingers 50. Furthermore, as the actuation assembly 60 is moved inwardly towards the actuated orientation, the structure of the release elements 62 tend to compress the tips of the fingers 50. Finally, when actuation assembly 60 generally reaches its actuated orientation, the fingers 50 are pressed sufficiently towards one another, and in the case of only one finger, inwardly, such that the depending protrusions 52 no longer abut the engagement hub 44, and the lancet 30 is released from the cocked orientation. At this point, the tension that has been maintained in the biasing element 42 drives the lancet 30 and in particular the piercing tip 32 through the piercing opening 26 to effectuate the prick of the patient.

As previously indicated, a concern associated with the utilization of lancet devices relates to the re-use of contaminated and/or used lancets. As such, the present invention further includes a restrictor assembly. The restrictor assembly is structured to substantially prevent the actuation assembly 60 from moving out of its actuated orientation, as in FIG. 3, at least after the lancet 30 has moved into the piercing orientation, if only for a temporary period of time. Moreover, and more precisely, the restrictor assembly of the illustrated embodiment ensures that once the actuation assembly 60 has moved into actuated orientation, it cannot return to the un-actuated orientation under normal circumstances. For example, the restrictor assembly preferably includes an abutment structure that is cooperatively disposed between the housing 20 and the release element 62 of the actuation assembly 60. In this regard, it is abutment structure that affirmatively prevents the actuation assembly 60 from moving back into the un-actuated orientation after movement into the actuated orientation. Specifically, once the single use lancet device 10 of the present invention has been fired by manipulation of the actuation assembly 60, even if a user wishes to cock the lancet 30 towards, and even possibly into, the cocked orientation, the actuation assembly 60 can no longer function to release the lancet 30 from that cocked orientation and result in a subsequent firing of the lancet 30. As such, only a single triggering of the actuation assembly 60 can be achieved, and only a single firing of the single use lancet device 10 of the present invention can be provided.

Looking in greater detail to the abutment structure of the restrictor assembly, in the illustrated embodiment, it includes a shoulder element and a restrictor panel. Furthermore, in the illustrated embodiment the shoulder element 64 is provided on each of the one or more release elements 62, and the restrictor panel 66 is defined in association with the housing 20. Looking first to the positioning of the actuation assembly 60 in an un-actuated orientation, as in FIG. 2, the shoulder element 64 of the release element 62 is disposed in such a position that it is not engaged with the restrictor panel 66. Although the shoulder element 62 may be disposed in a variety of orientations, in the illustrated embodiment, for convenient and stability of use, the shoulder element 64 is disposed within one or more corresponding recesses 68 defined in the housing 20 when the actuating assembly 60 is disposed in the un-actuated orientation. Further, these recesses 68 may include an at least partially tapered configuration that may correspond to a similar configuration on the release elements 62 so as to define a mating and/or tapered orientation between the release element 62 and the retention panel 66. Accordingly, and based on the partially biased configuration of the release element(s) 62, as the actuation assembly 60 is pushed inwardly towards it actuated orientation, the confronting sloped surfaces and/or a single sloped surface, result in a general compression of the release element 62 towards a central axis, allowing for the free movement of the actuation assembly 60 inwardly and into the actuated orientation. It is also seen in some embodiments that this compression may further facilitate the release of the lancet 30 from the cocked orientation.

Once the actuation assembly 60 has moved into the actuated orientation, as in FIG. 3, preferably at least due to the tendency of the release element(s) 62 to spread generally outward, the shoulder element 64 abuts the retention panel 66 and outward passage and/or movement of the actuation assembly 60 back into the un-actuated orientation cannot result. Indeed, even if the lancet 30 were moved back into the cocked orientation and/or into engaging relation with actuation assembly 60, and in particular the release element 62, such would merely serve to further expand the releasing element(s) 62 and would not function to achieve a compression necessary to allow for removal of the actuation assembly 60 into the un-actuated orientation. Accordingly, once the actuation assembly 60 has been used to fire the single use lancet device 10, it cannot be used again to achieve subsequent firing. Of course, it is recognized that a variety of other configurations may be provided for the restrictor assembly so as to allow the actuation assembly 60 to effectively move into the actuated orientation, performing its task of releasing the lancet 30 from its cocked orientation, but not allowing the actuation assembly 60 to subsequently return to the un-actuated orientation. Also, it is recognized that although it is generally not preferred for the aforementioned reasons, some structure to release the actuation assembly 60 may be provided so as to allow it to move back into the un-actuated orientation, such as in the case of inadvertent triggering without the lancet 30 having been in the cocked orientation.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A single use lancet device comprising:
   a) a housing;
   b) a lancet, said lancet including a piercing tip;
   c) said lancet movably disposed in said housing and structured to move at least between a cocked orientation and a piercing orientation;
   d) a driving assembly structured to move said lancet at least temporarily into said piercing orientation;
   e) an actuation assembly structured to move between an actuated and an un-actuated orientation, movement of said actuation assembly into said actuated orientation resulting in said movement of said lancet into said piercing orientation; and
   f) a restrictor assembly structured to substantially prevent said actuation assembly from moving out of said actuated orientation at least after said lancet has moved at least temporarily into said piercing orientation by said drive assembly.

2. The single use lancet device recited in claim 1 further comprising a retention member; and an engagement hub, said engagement hub structured to be cooperatively engaged with said retention member at least upon said lancet being disposed in said cocked orientation so as to maintain said lancet in said cocked orientation until said retention member is affirmatively released from said cooperative engagement therewith.

3. The single use lancet device recited in claim 2 wherein said actuation assembly is structured and disposed to release said retention member from said cooperative engagement with said engagement hub.

4. The single use lancet device recited in claim 3 wherein said retention member includes at least one finger, said finger including a depending protrusion structured to engage cooperative structure on said engagement hub when said lancet is disposed in said cocked orientation, said actuation assembly being structured to at least temporarily urge said finger out of said engagement with said cooperative structure on said engagement hub.

5. The single use lancet device recited in claim 1 further comprising a cocking assembly, said cocking assembly being operatively associated with said lancet and structured to move said lancet into said cocked orientation.

6. The single use lancet device recited in claim 5 wherein said cocking assembly is structured to protrude from said housing.

7. The single use lancet device recited in claim 5 wherein said cocking assembly is integrally formed with said lancet.

8. The single use lancet device recited in claim 5 wherein said cocking assembly includes a cocking element structured to extend into said housing and into movement engagement with said lancet.

9. The single use lancet device recited in claim 8 wherein said cocking element protrudes from a side of said housing so as to facilitate movement by a user's finger.

10. The single use lancet device recited in claim 1 wherein said lancet is structured to be maintained in said cocked orientation until released by said actuation assembly.

11. The single use lancet device recited in claim 10 wherein said actuation assembly includes a release element structured to release said lancet from said cocked orientation.

12. The single use lancet device recited in claim 11 wherein said restrictor assembly includes an abutment structure cooperatively disposed between said housing and said release element, and structured to prevent said actuation assembly from moving into said un-actuated orientation after movement into said actuated orientation.

13. The single use lancet device recited in claim 12 wherein said abutment structure comprises a shoulder element and a restrictor panel, said restrictor panel and said shoulder element structured to pass one another upon said actuation assembly moving from said un-actuated orientation to said actuated orientation, and to abut one another upon attempted movement of said actuation assembly into said un-actuated orientation after movement into said actuated orientation.

14. The single use lancet device recited in claim 13 wherein said shoulder element includes an at least partially biased configuration structured to at least partially retract to facilitate passage of said restrictor panel and said shoulder element past one another in a first direction corresponding movement of said actuation assembly into said actuated orientation from said un-actuated orientation, and to expand subsequent said passage past one another in said first direction such that said shoulder element and said restrictor panel abut one another upon movement towards one another in a second direction generally opposite said first direction.

15. The single use lancet device recited in claim 13 wherein said shoulder element is defined on said release element of said actuation assembly lancet, and said restrictor panel is defined in said housing.

16. The single use lancet device recited in claim 1 wherein said driving assembly includes a biasing element operatively disposed between said lancet and said housing.

17. The single use lancet device recited in claim 16 wherein said biasing element comprises a spring.

18. A single use lancet device comprising:
   a) a housing;
   b) a lancet, said lancet including a piercing tip;
   c) said lancet movably disposed in said housing and structured to move at least between a cocked orientation and a piercing orientation;
   d) a driving assembly structured to move said lancet at least temporarily into said piercing orientation;
   e) a retention member and an engagement hub, said engagement hub structured to be cooperatively engaged with said retention member at least upon said lancet being disposed in said cocked orientation so as to maintain said lancet in said cocked orientation until said retention member and said engagement hub are released from said cooperative engagement with one another;

f) an actuation assembly structured to move between an actuated and an un-actuated orientation, movement of said actuation assembly into said actuated orientation structured to release said retention member and said engagement hub from said cooperative engagement with one another and thereby result in movement of said lancet into said piercing orientation;

g) a restrictor assembly structured to substantially prevent said actuation assembly from moving out of said actuated orientation at least after said lancet has moved at least temporarily into said piercing orientation; and h) said restrictor assembly includes an abutment structure cooperatively disposed between said housing and said actuation assembly, and structured to prevent said actuation assembly from moving into said un-actuated orientation after movement into said actuated orientation.

* * * * *